(12) United States Patent
Welp

(10) Patent No.: US 8,770,445 B2
(45) Date of Patent: Jul. 8, 2014

(54) FLUID DISCHARGE HEAD

(75) Inventor: Gisbert Welp, Sundern (DE)

(73) Assignee: MeadWestvaco Calmar GmbH, Hemer (DE)

(*) Notice: Subject to any disclaimer, the term of this patent is extended or adjusted under 35 U.S.C. 154(b) by 349 days.

(21) Appl. No.: 12/997,099

(22) PCT Filed: May 26, 2009

(86) PCT No.: PCT/EP2009/003722
§ 371 (c)(1),
(2), (4) Date: Dec. 9, 2010

(87) PCT Pub. No.: WO2009/149826
PCT Pub. Date: Dec. 17, 2009

(65) Prior Publication Data
US 2011/0089197 A1    Apr. 21, 2011

(30) Foreign Application Priority Data
Jun. 10, 2008   (DE) .......................... 10 2008 027 599

(51) Int. Cl.
B65D 88/54           (2006.01)
(52) U.S. Cl.
USPC ...................... 222/321.6; 222/321.9; 222/340
(58) Field of Classification Search
USPC ........ 222/321.6, 321.1, 321.2, 321.3, 189.11, 222/321.8, 340, 341, 321.9, 394, 375, 380, 222/321.5, 321.7; 239/570, 572, 571, 576
See application file for complete search history.

(56) References Cited

U.S. PATENT DOCUMENTS

| | | | |
|---|---|---|---|
| 4,183,449 A | | 1/1980 | Blake |
| 4,640,443 A * | | 2/1987 | Corsette ...................... 222/321.3 |
| 4,830,284 A | | 5/1989 | Maerte |
| 4,991,747 A * | | 2/1991 | Van Brocklin ............. 222/321.3 |
| 5,988,449 A * | | 11/1999 | Fuchs et al. ............... 222/189.11 |
| 6,059,151 A * | | 5/2000 | Fuchs ......................... 222/321.6 |
| 6,062,433 A | | 5/2000 | Fuchs |
| 6,189,739 B1 | | 2/2001 | Schuckmann |
| 6,250,509 B1 * | | 6/2001 | Fuchs ......................... 222/321.6 |
| 6,308,867 B1 | | 10/2001 | Wolter |
| 7,182,226 B2 * | | 2/2007 | Mbonyumuhire ......... 222/321.7 |
| 7,201,296 B2 * | | 4/2007 | Graf ........................... 222/321.9 |

(Continued)

FOREIGN PATENT DOCUMENTS

| | | |
|---|---|---|
| DE | 3315334 | 10/1984 |
| DE | 19622124 | 12/1997 |

(Continued)

*Primary Examiner* — Kevin P Shaver
*Assistant Examiner* — Stephanie E Williams
(74) *Attorney, Agent, or Firm* — MWV Intellectual Property Group

(57) ABSTRACT

Fluid discharge head having a discharge nozzle which can be placed on a discharge device and which holds a medium guide and a medium outlet at the end of a medium guide, in the region of the medium outlet a movable closure element that can be moved into an open position is provided and, for the purpose of actuating discharge, the discharge nozzle and the discharge device can be moved axially towards each other, for which purpose the discharge nozzle has a skirt to form a sliding guide with a section on the discharge device, the skirt (9) of the discharge nozzle (5) being assigned a second, additional skirt (12) in order to form an annular bush (13) which can be mounted such that it can be displaced longitudinally on a section (11) of the discharge device (2) that is formed as an annular shaft.

4 Claims, 2 Drawing Sheets

(56) References Cited

U.S. PATENT DOCUMENTS

Figure 1:
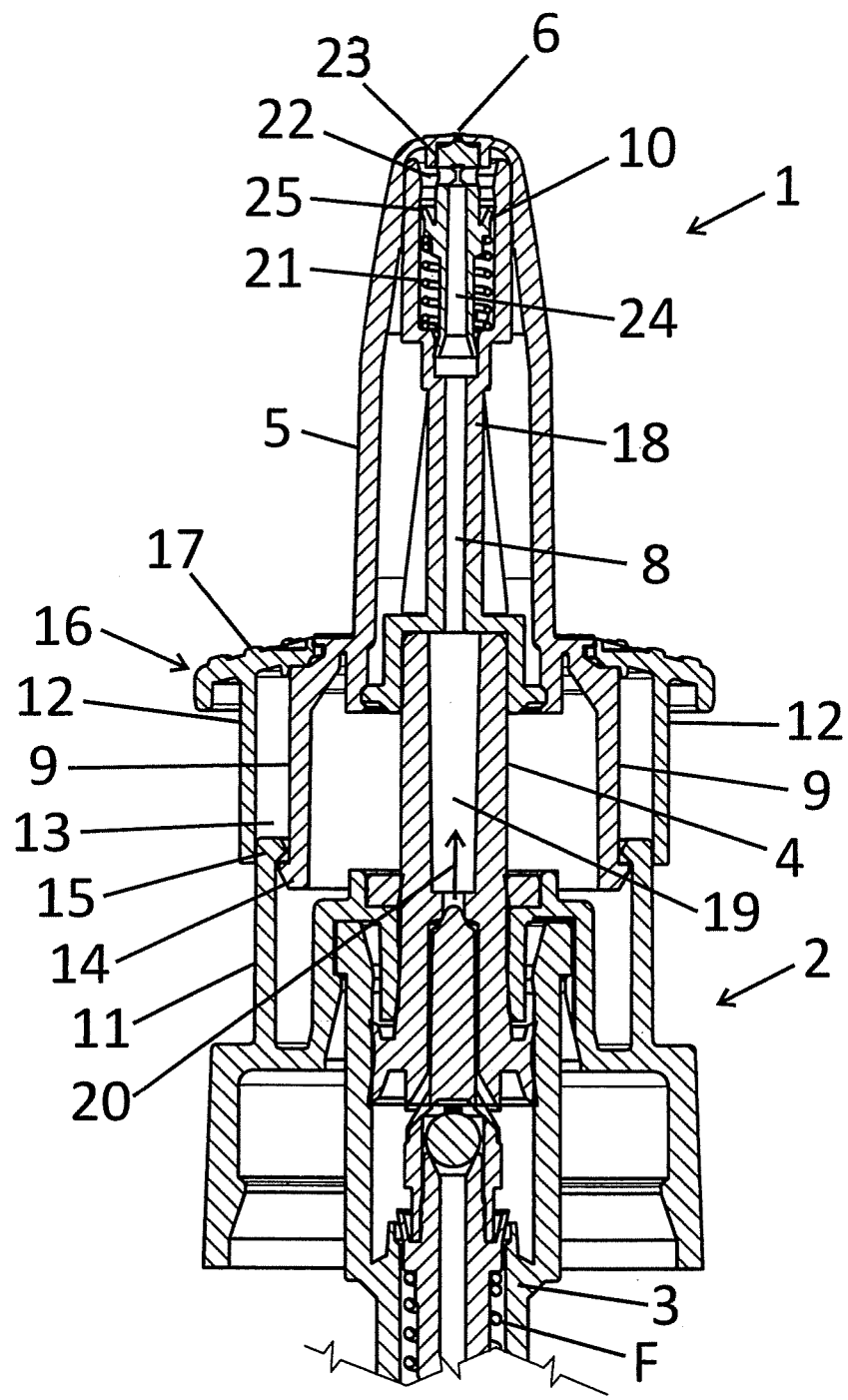

| | | |
|---|---|---|
| 7,726,522 B2 * | 6/2010 | Greiner-Perth ............ 222/321.6 |
| 7,828,231 B2 | 11/2010 | Harms |
| 2003/0183655 A1 * | 10/2003 | Padar ......................... 222/321.9 |
| 2004/0256414 A1 * | 12/2004 | Graf ............................ 222/321.1 |
| 2006/0186141 A1 * | 8/2006 | Greiner-Perth ............ 222/321.6 |
| 2007/0262090 A1 | 11/2007 | Ritsche |
| 2011/0084100 A1 | 4/2011 | Welp |

FOREIGN PATENT DOCUMENTS

| | | |
|---|---|---|
| DE | 298 11 242 | 11/1999 |
| DE | 10 2004 050679 | 4/2006 |
| EP | 0901836 | 3/1999 |
| WO | WO2007009617 | 1/2007 |
| WO | WO2009149825 | 12/2009 |

* cited by examiner

FLUID DISCHARGE HEAD

CROSS-REFERENCE TO RELATED APPLICATIONS

This application claims the benefit of German Application No. 102008027599.9, entitled "Fluidaustragkopf," filed 10 Jun. 2008, and of International Application Number PCT/EP09/003722, entitled "Fluidaustragkopf," filed 26 May 2009, and incorporates each of those applications herein by reference in their entireties.

The invention relates to a fluid discharge head.

WO2007/009617 A1 discloses a fluid discharge head having a discharge nozzle which has a discharge opening and which holds an inner sleeve. Arranged in the inner sleeve is an inner body, which delimits an outlet duct and has a connecting element for providing a connection to the mating piece of a discharge device. At the end adjacent to the discharge opening, the inner sleeve has a sealing face, against which a valve plug located on the inner body and closing the outlet duct is spring-pre-stressed. Therefore, a valve is integrated into the discharge head, in which the valve closure is implemented by a relative movement when actuated by the user. For this purpose, fluid discharge head and discharge device can be moved axially towards each other. When the actuating force is released, the units return to the initial position in the opposite direction by means of a spring. Additionally provided is an anti-removal safeguard, which ensures that fluid discharge head and discharge device are not separated from each other counter to the actuating direction.

For this purpose, the anti-removal safeguard has an annular snap-in cam and a shell on a discharge nozzle of the fluid discharge head. The disadvantage is that the anti-removal safeguard is located completely within a housing of the fluid discharge head. The housing has a cap shell which projects a long way and which impairs the ability of the dispenser assembled from the fluid discharge head and discharge device to be handled.

It is therefore an object of the invention to devise a fluid discharge head which permits improved handling.

This object is achieved by the features of claim 1.

In this way, a fluid discharge head is devised in which an additional, second skirt improves the guidance of the fluid discharge head with respect to the discharge device, specifically in conjunction with an anti-removal safeguard. The anti-removal safeguard is therefore integrated into a guide element which steers the axial movement of fluid discharge head and discharge device in relation to each other during an actuation of the dispenser assembled from them.

Further refinements of the invention can be gathered from the following description and the subclaims.

The invention will be explained in more detail below by using the exemplary embodiment illustrated in the appended figures.

Figure 2:
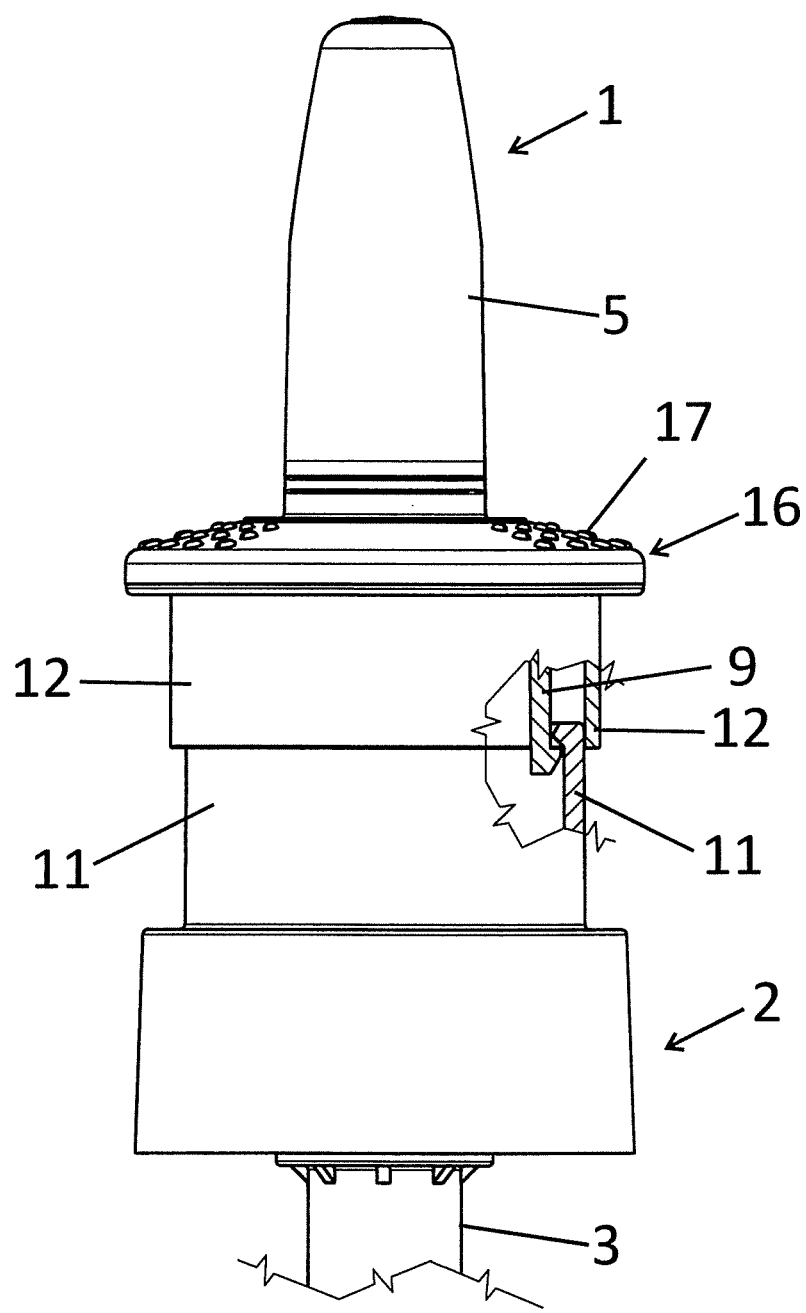

FIG. 1 shows, schematically in section, a fluid discharge head with a portion of a discharge device, FIG. 2 shows the two units according to FIG. 1 in a broken-open illustration.

The invention relates to a fluid discharge head 1 for use with a discharge device 2, the discharge device 2 comprising a medium store, not shown, for fluid, in which the medium is placed under pressure or from which the medium is discharged via a medium pump 3, in particular a thrust piston pump. The discharge device 2 preferably has a mating piece 4, to which the fluid discharge head 1 can be fitted.

The discharge device 2 with fluid discharge head 1 put in place forms a dispenser for in particular liquid media.

The fluid discharge head 1 and the discharge device 2 can be moved axially towards each other for the purpose of discharge actuation, while shortening the dispenser. When an actuating force is released, they return back in the opposite direction to the initial position according to FIG. 1 by means of a spring F.

The fluid discharge head 1 has a discharge nozzle 5 which can be placed on the discharge device 2 and which holds a medium guide 8 in the form of a medium duct and a medium outlet having a discharge opening 6 at the end of a medium guide 8. Provided in the region of the medium outlet is a movable closure element 10 which can be moved into an open position and which is preferably formed as a spring-pre-stressed valve body.

The discharge nozzle 5 has a skirt 9 to form a sliding guide with a section 11 on the discharge device 2. This skirt 9 of the discharge nozzle 5 is assigned a second, additional skirt 12 in order to form an annular bush 13. The annular bush 13 can be mounted such that it can be displaced longitudinally in the axial direction on a section 11 of the discharge device 2 that is formed as an annular shaft. The second, additional skirt 12 is preferably formed so as to be radially springy. To this end, the second, additional skirt 12 can be shorter than the other skirt 9. The second, additional skirt is preferably formed so as to be shorter in such a way that a radial snap-in ramp is formed between the two skirts 9, 12.

The second, additional skirt 12 is preferably an outer skirt 12, while the other skirt 9 is an inner skirt 9. A cam 14 preferably projects into the annular bush 13 for an anti-removal safeguard. The cam 14 is preferably provided as a cam edge on the inner skirt 9. A mating cam 15 to the cam 14 is formed on the section 11.

It is further preferred for a push-on part 16 having a grip surface 17 to be provided on the nozzle 5. The second, additional skirt 12 is then preferably formed on this push-on part 16. The push-on part 16 can be fabricated from a different material from that of the discharge nozzle 5. In this way, there is the possibility of fabricating the two skirts 9, 12 from different materials. In particular, the second, additional skirt 12 can consist of a softer plastic than the other skirt 9.

The discharge nozzle 5 preferably holds an inner sleeve 18, which delimits the medium duct 8, which adjoins a discharge section 19 of the medium guide 20 in the form of duct sections and/or medium spaces adjoining one another and located within the fluid discharge head 1.

At its end facing the discharge opening 6, the inner sleeve 18 is shaped like a pot. In order to close the discharge opening 6, the inner sleeve 18 holds a spring-loaded valve body 10 automatically closing the discharge opening 6 in this pot-shaped end.

The valve body 10 is formed as a cylindrical piston, which closes the discharge opening 6 as a spring-loaded valve body 10 with a pre-stressing force from a compression spring 21. The valve body 10 has an intermediate valve plate 25, which seals off a pressure chamber 22 connected to the medium duct 8 with respect to an upper valve seat 23 of the valve body 10. The intermediate valve plate 25 is preferably additionally used to guide the movement of the valve body 10.

In order to open the upper valve seat 23, a medium discharge pressure which is higher than a spring force from the compression spring 21 that holds the valve body 10 closed can be set in the pressure chamber 22. FIG. 1 shows a discharge opening 6 closed by the valve body 10.

Medium flows through the valve body 10, for which purpose the valve body 10 has a passage duct 24 which connects the medium duct 8 to the pressure chamber 22.

The discharge nozzle 5 here has the form of a nasal olive, in order to be able to be placed on the mating piece 4 as a nasal adapter. For other applications, the discharge nozzle 5 can have other external contours.

The invention claimed is:

1. A fluid discharge device, comprising:
a fluid discharge head, comprising:
- a discharge nozzle;
- a discharge opening in one end of the discharge nozzle;
- a skirt at an opposite end of the discharge nozzle;
- a cam extending outward from an end of the skirt;
- an upper valve seat adjacent the discharge opening;
- an inner sleeve seated in the discharge nozzle and having a pot-shaped end adjacent the upper valve seat;
- a medium guide through the inner sleeve;
- a valve body seated in the pot-shaped end of the inner sleeve, comprising:
  - a cylindrical piston;
  - a passage duct through the cylindrical piston in communication with the medium guide; and
  - an intermediate valve plate engaged with the inner sleeve;
- a pressure chamber defined by the valve body and inner sleeve;
- a compression spring seated in the pot-shaped end of the inner sleeve and in contact with the valve body, wherein the compression spring holds the valve body against the upper valve seat;

a discharge device coupled to the discharge head, comprising:
- a medium pump attached to the discharge device;
- a mating piece assembled with the medium pump;
- a discharge section through the mating piece;
- a section extending towards the fluid discharge head;
- a mating cam extending inwardly from an end of the section; and
- wherein the mating piece is fitted to the fluid discharge head and the discharge section is in communication with the medium guide through the inner sleeve;

a push on part attached to the discharge nozzle and having a second skirt extending downward from the discharge nozzle towards the discharge device; and
wherein the skirt and the second skirt define an annular bush and the section is positioned in the annular bush between the skirt and the second skirt; and
wherein the discharge section, medium guide and passage duct provide a substantially linear pathway through the fluid discharge device.

2. The fluid discharge device of claim 1, wherein the push on part comprises a material that is different than the material of the discharge nozzle.

3. The fluid discharge device of claim 1, wherein the push on part comprises a soft plastic material.

4. The fluid discharge device of claim 1, wherein the push on part further comprises a grip surface.

* * * * *